United States Patent
Roscioli et al.

(10) Patent No.: US 9,523,666 B2
(45) Date of Patent: Dec. 20, 2016

(54) TECHNIQUES FOR ACTIVE PASSIVATION

(71) Applicant: Aerodyne Research, Inc., Billerica, MA (US)

(72) Inventors: Joseph R. Roscioli, Chelmsford, MA (US); Scott C. Herndon, Littleton, MA (US); David D. Nelson, Jr., N. Chelmsford, MA (US)

(73) Assignee: Aerodyne Research, Inc., Billerica, MA (US)

( * ) Notice: Subject to any disclaimer, the term of this patent is extended or adjusted under 35 U.S.C. 154(b) by 211 days.

(21) Appl. No.: 14/570,401

(22) Filed: Dec. 15, 2014

(65) Prior Publication Data

US 2016/0169852 A1    Jun. 16, 2016

(51) Int. Cl.
| | |
|---|---|
| G01N 33/00 | (2006.01) |
| G01N 27/00 | (2006.01) |
| G01J 3/10 | (2006.01) |
| G01N 1/20 | (2006.01) |
| G01N 27/414 | (2006.01) |
| C12M 1/34 | (2006.01) |
| B01J 19/00 | (2006.01) |

(52) U.S. Cl.
CPC ............ G01N 33/006 (2013.01); G01J 3/108 (2013.01); G01N 33/0037 (2013.01); G01N 33/0054 (2013.01); B01J 19/002 (2013.01); B01J 2219/02 (2013.01); C12M 41/32 (2013.01); G01J 2003/102 (2013.01); G01N 27/4141 (2013.01); G01N 27/4145 (2013.01); G01N 33/0062 (2013.01)

(58) Field of Classification Search
CPC ............ G01N 27/4141; G01N 27/4145; G01N 33/006; G01N 33/0054; G01N 33/0062; G01N 33/0037; B01J 19/002; B01J 2219/02; C12M 41/32; G01J 3/108
See application file for complete search history.

(56) References Cited

U.S. PATENT DOCUMENTS

| | | | |
|---|---|---|---|
| 2007/0086915 A1* | 4/2007 | LeBoeuf | G01N 21/6428 422/400 |
| 2015/0020577 A1* | 1/2015 | Luebke | G01N 27/12 73/31.06 |

OTHER PUBLICATIONS

Ellis, R.A. et al., "Characterizing a Quantum Cascade Tunable Infrared Laser Differential Absorption Spectrometer (QC-TILDAS) for measurements of atmospheric ammonia", Atmospheric Measurement Techniques, 3, pp. 397-406, Mar. 30, 2010.

(Continued)

*Primary Examiner* — Jennifer Wecker
(74) *Attorney, Agent, or Firm* — Cesari and McKenna, LLP; James A. Blanchette (57) ABSTRACT

In one embodiment, active (continuous or intermittent) passivation may be employed to prevent interaction of sticky molecules with interfaces inside of an instrument (e.g., an infrared absorption spectrometer) and thereby improve response time. A passivation species may be continuously or intermittently applied to an inlet of the instrument while a sample gas stream is being applied. The passivation species may have a highly polar functional group that strongly binds to either water or polar groups of the interfaces, and once bound presents a non-polar group to the gas phase in order to prevent further binding of polar molecules. The instrument may be actively used to detect the sticky molecules while the passivation species is being applied.

23 Claims, 10 Drawing Sheets

(56) References Cited

OTHER PUBLICATIONS

Lee, B.H. et al., "Simultaneous measurements of atmospheric HONO and NO2 via absorption spectroscopy using tunable mid-infrared continuous-wave quantum cascade lasers", Applied Physics B, vol. 102, Issue 2, pp. 417-423, Oct. 20, 2010.
McManus, J.B. et al., "Astigmatic mirror multipass absorption cells for long-path-length spectroscopy", Applied Optics, vol. 34, No. 18, pp. 3336-3348, Jun. 20, 1995.
Neuman, J.A. et al., "Study of Inlet Materials for Sampling Atmospheric Nitric Acid", Environmental Science and Technology, vol. 33, No. 7, pp. 1133-1136, Feb. 13, 1999.
Ulman, Abraham, "Formation and Structure of Self-Assembled Monolayers", Chemical Reviews, vol. 96, No. 4, pp. 1533-1554, Apr. 18, 1996.
Xue, Chao-Hua et al., "Large-area fabrication of superhydrophobic surfaces for practical applications: an overview", Science and Technology of Advanced Materials, vol. 11, No. 3, 16 pages, Jun. 2010.

\* cited by examiner

TECHNIQUES FOR ACTIVE PASSIVATION

STATEMENT REGARDING FEDERALLY SUPPORTED RESEARCH

This invention was made with Government support under DE-SC0006193 awarded by the Department of Energy. The Government has certain rights in this invention.

BACKGROUND

1. Technical Field

The present disclosure relates generally to measurement of sticky molecules, and more specifically to techniques for preventing interaction of sticky molecules with interfaces inside of an instrument.

2. Background Information

Measurement of Nitric acid ($HNO_3$), ammonia ($NH_3$) and other polar molecules has proven increasingly important in the understanding of atmospheric processes. Their large dipole moments and hydrophilic properties are primary factors in their nucleation and condensation roles in atmospheric aerosol formation. For example, nitric acid is an important photochemical product during $NO_x$ oxidation and is an important test of our understanding of modeled photoreactivity in the atmosphere. However, the large dipoles and hydrophilic properties of these polar molecules render them difficult to detect on timescales less than approximately 1 minute. These polar molecules may not only be "sticky" upon interfaces (i.e. surfaces forming a common boundary among two different phases) inside of an instrument (e.g., an infrared absorption spectrometer) by virtue of their own interactions with polar surface groups, but may also be attracted to any points where adsorbed or liquid water accumulates. In light of their properties, $HNO_3$ and $NH_3$ may be considered "sticky molecules". As used herein, the term "sticky molecule" refers to the class of polar molecules having large dipole moments and hydrophilic properties that cause them to temporarily bind to interfaces. In addition to $HNO_3$ and $NH_3$, formaldehyde ($CH_2O$), acetone ($C_3H_6O$), as well as other molecules that act as a Lewis acid or a Lewis base may be considered sticky molecules.

The consequence of the interactions of sticky molecules with interfaces inside of instruments may be significantly lengthened response time of an output signal to rapid changes in concentration, which in some cases may increase detection times to 10-100 seconds(s). For reference, measurements of non-sticky molecules, such as $CH_4$, $CO_2$ and $N_2O$, are typically limited by the sampling flow rate through the instrument and the associated detection volume, and can therefore often achieve detection times less than 0.2 s.

Previous attempts to address the issue of lengthened response time and reduced detection bandwidth have included using materials with non-polar chemical groups, or chemically coating surfaces with permanent non-polar surfactants, which may reduce aggregation of both water and other dipolar species. The surface materials, for example PolyTetraFluoroEthylene (PTFE) or PerFluoroAlkoxy (PFA), or the coatings, for example fluorinated alkylsiloxanes, are generally applied during instrument configuration or manufacture. Such techniques may, at least initially, improve response time. However, the effects typically diminish over the course of instrument usage. An interface that is initially pristine is compromised when as little as a single monolayer of salt or inorganic matter coats the interfaces. Thus, the response time of the instrument may gradually become slower, as an increasing fraction of the interfaces becomes coated in adsorptive matter. One may attempt to clean the interfaces with solvents, to try to restore some of the initial benefits. However, recoating or cleaning or recoating generally involves discontinuing use of the instrument, bringing any internal vacuum to atmospheric pressure, and potentially disassembling significant portions of the instrument. Considerable instrument downtime may be incurred.

Further, coating interfaces with PTFE or PFA often leads to response times that are highly dependent upon relative humidity. The presence of water at the interfaces may be a primary factor behind the "stickiness". Attempts have been made to lightly heat portions of instruments, to attempt to remove water. However, such an approach may not successfully remove all water because of a) the possibly strong binding between water and the surface, which could be larger than the water-water interaction, and b) the presence of small crevices and pockets in all but the most pristine surfaces, which could be difficult to evacuate with heat. It would be desirable to find a technique that was not so highly dependent on humidity and trapped water.

Accordingly, there is a need for improved techniques for preventing interaction of sticky molecules with interfaces inside of an instrument.

SUMMARY

In one example embodiment, continuous passivation may be employed to prevent interaction of sticky molecules with interfaces inside of an instrument (e.g., an infrared absorption spectrometer). A passivation species may be continuously applied to an inlet (e.g., a particle separation inlet) of the instrument while a sample gas stream is being applied. The passivation species has a highly polar functional group that strongly binds to either water or polar groups of the interface, and once bound presents a non-polar group to the gas phase in order to prevent further binding of polar molecules. The instrument may be actively used to detect sticky molecules while the passivation species is being applied. In this manner, a continuously renewed coating may be provided during ongoing instrument use, whose effectiveness is maintained over time.

In another example embodiment, intermittent passivation is employed to prevent interaction of sticky molecules with interfaces inside of an instrument. A passivation species is applied to the inlet for a first period of time, while the sample gas stream is being applied, to build a protective coating on the interfaces. The passivation species is then withheld during a second period of time, during which the built protective coating continues to prevent interaction of sticky molecules with the interfaces. The process may be repeated in a cyclical manner to maintain sufficient coating on the interfaces to prevent interaction of sticky molecules with the interfaces. In this manner, a renewed coating may be provided that is periodically renewed during ongoing instrument use, so that its effectiveness is maintained.

The passivation species may be selected based on the sticky molecule being detected. For example, for $HNO_3$ the passivation species may be selected as perfluoroheptanoic acid (PFHpA), perfluorooctanoic acid (PFOA), or perfluorobutane sulfonic acid (PFBSA), or another species. Likewise, for $NH_3$ the passivation species may be selected as 1H,1H-perfluorooctylamine (PFOAm) or another species. Continuous passivation or intermittent passivation may be utilized with a variety of types of inlets of the instrument, which include particle separator inlets containing, for example, a virtual impactor, a cyclone particle separator, or a PTFE membrane particle filter. Further, the passivation species may be applied to the inlet of the instrument in various different manners. In one implementation, the passivation species may be introduced into a stream of air, for example, by bubbling the stream of air through a gas bubbler that contains a liquid passivation species or passing the stream of air over a solid passivation species within the gas bubbler. In another implementation, the sample gas stream may be bubbled or passed through the gas bubbler that contains the passivation species. In still another implementation, the passivation species may be injected through a calibration port of the inlet.

It should be understood that the example embodiments and implementations discussed in this Summary may include a variety of other features, including other features discussed below, and variations thereof. Further a variety of other example embodiments may be utilized. This Summary is intended simply as a brief introduction to the reader, and does not imply that the specific features mentioned herein are all the features of the invention, or are essential features of the invention.

BRIEF DESCRIPTION OF THE DRAWINGS

The description below refers to the accompanying drawings of example embodiments, of which.

DETAILED DESCRIPTION OF AN ILLUSTRATIVE EMBODIMENT

Instrument Configuration

Figure 1:
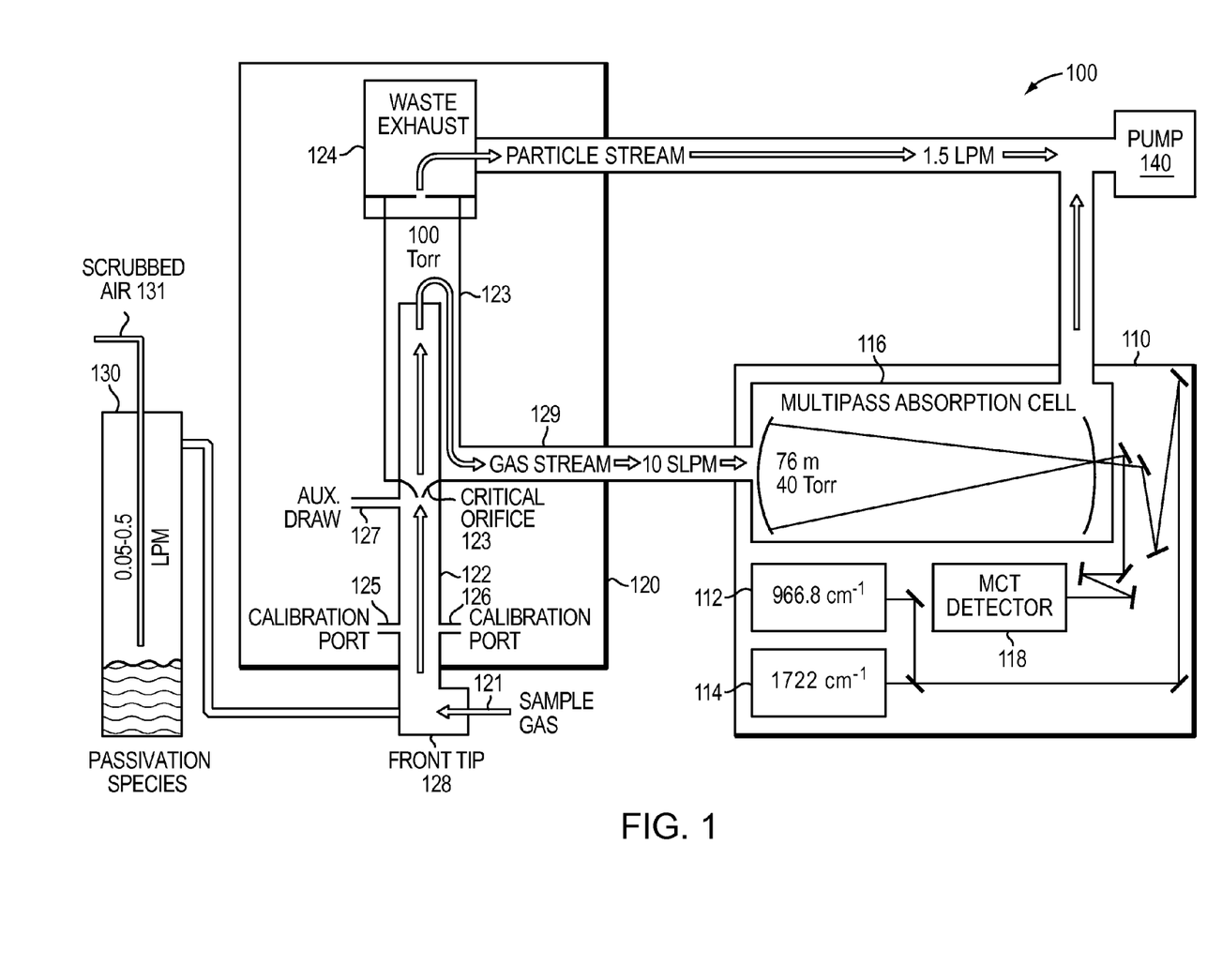
FIG. 1 is a diagram depicting an example instrument, configured for active (continuous or intermittent) passivation to prevent interaction of sticky molecules with interfaces inside of an instrument.

FIG. 1 is a diagram depicting an example instrument 100, configured for active (continuous or intermittent) passivation to prevent interaction of sticky molecules with interfaces inside of the instrument. In the example shown, the instrument 100 is an infrared absorption spectrometer having certain types of components as detailed below. However, it should be understood that the instrument 100 may alternatively be another type of instrument having different components.

The instrument 100 may be generally divided into a detection system 110, a particle separation inlet 120, and a passivation species delivery system 130. In the example shown in FIG. 1, the detection system 110 is a dual-quantum cascade laser (QCL) detection system that provides a path length of 76 m. The two QCL lasers 112, 114 may be tuned to lines pertinent to the sticky molecules being detected, for example, the 966.8 $cm^{-1}$ lines of $NH_3$ and the 1722.5 $cm^{-1}$ lines of $HNO_3$. The lasers may be used with a multi-pass absorption 116 cell, of a modified astigmatic Herriot design (or another design), and a mercury cadmium telluride (MCT) detector 118 (or another type of detector). The absorption cell 116 may receive an incoming gas stream 129, for example a 10 standard liter per minute (SLPM) gas stream, and exhaust gas that has already undergone analysis via a passage to a pump 140. Cell pressures may be adjusted to approximately 40 Torr (or other desired pressures) by choking the pump 140, using a ball valve, upstream pressure controller, or other similar mechanism (not shown). Such an arrangement may provide, for example, 1-s sensitivities of 90 parts per trillion by volume (pptv) for $NH_3$ and 130 pptv for $HNO_3$.

In the example shown in FIG. 1, the particle separation inlet 120 coupled to the detector 110 is an inertial inlet (a form of virtual impactor). In such an inlet, a sample gas stream 121 (including some particulates) may enter via a front tip 128, and be passed via a glass tube 122 to a critical orifice 123. The glass tube 122 may include glass calibration ports 125, 126 and an auxiliary draw 127. After passing through the critical orifice 123, the sample gas (and particulates) are accelerated to a higher speed at a lower pressure (approximately 100 Torr). These molecules are passed into a second glass tube 123, where the gas stream must make a turn, e.g., a 180° turn, to continue. The radius of this turn may be too small for aerosol and dust particles with aerodynamic diameters greater than 300 nm, which therefore pass into a waste exhaust chamber 124. In one implementation, where the sample gas stream is 14 SLPM, the waste exhaust may be approximately ⅐ of the total volume passing into the particle separation inlet 120, creating an approximately 2 liters per minute (LPM) particle stream that is exhausted via the pump 140. The time response of most inlets improves with increasing temperature, so here the inlet 100 may be heated and maintained, for example, to 60° C. Other than the glass inlet tubes 122, 123, PFA tubing may be used throughout the inlet 120, and the rest of the instrument 100.

While an inertial inlet is shown in FIG. 1, it should be understood that a variety of other types of inlets may alternatively be used. For example, in one alternative implementation, the particle separation inlet 120 may be a cyclone particle separator. The cyclone particle separator may, for example, be operated at 12.9 SLPM to provide a 0.6 μm particle separation cutpoint. A PFA critical orifice may be placed immediately downstream of the cyclone exit port, in order to establish critical flow. A PFA cross fitting may be placed upstream of the cyclone to provide a sample gas entrance port and calibration ports. In another alternative implementation, the particle separation inlet 120 may be a PTFE-membrane particle filter. The filter may, for example, be operated at 12.0 SLPM, with a PFA critical orifice placed downstream to establish the flow rate. Implementations that use a cyclone or a filter may be kept at room temperature or heated.

Figure 2A:
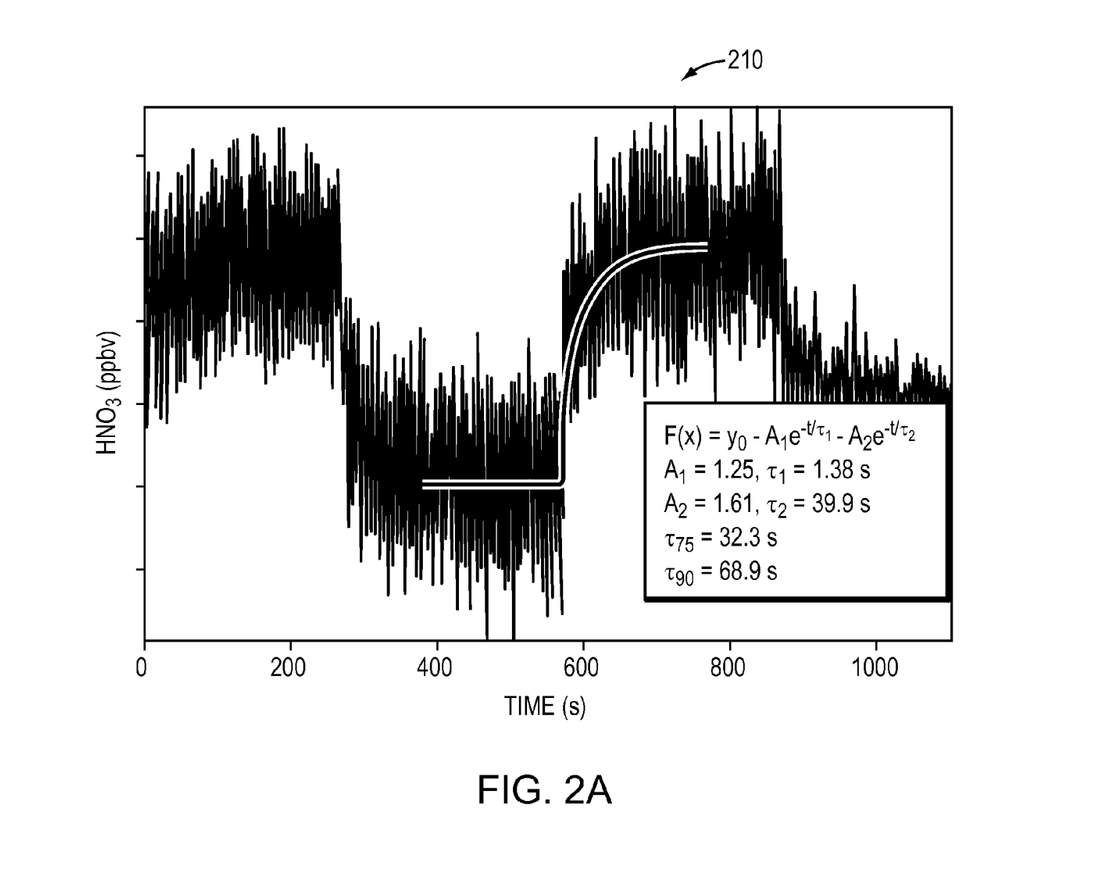
FIG. 2A shows a graph of typical $HNO_3$ response time using the example instrument of FIG. 1, absent a passivation agent.

A passivation species delivery system 130 may be coupled to the particle separation inlet 120. In the example shown in FIG. 1, the passivation species delivery system 130 includes a gas bubbler that contains a liquid passivation species, through which a stream of air 131 is bubbled. If the passivation species is a solid at operating temperature, the stream of air may be passed over the solid material within the bubbler. For example, while PFBSA and PFOAm are liquids at room temperature, PFOA and PFHpA are solids. The gas bubbler may be located outside of the particle separation inlet 120. The stream of air 131 may be between 2 and 500 standard cubic centimeters per minute (sccm) of dry, scrubbed air. The stream of air 131 now containing the passivation species may be entrain into the 14 SLPM sample gas stream 121 at the front tip 128 of the particle separation inlet 120.

It should be understood that a variety of other passivation species delivery systems 130 may alternatively be used. For example, in one alternative implementation, the entire sample gas stream 121 may be bubbled or passed through a gas bubbler that contains the passivation species. In still another alternative implementation, the passivation species delivery system 130 may inject the passivation species through a calibration port 125, 126 of the particle separation inlet 120. In such an alternative, a gas bubbler that contains the passivation species may be located inside of an enclosure of the particle separation inlet 120 (and possibly heated, e.g., to 60° C.), and a small flow (e.g., 2-100 sccm) introduced via the calibration port.

Use of the passivation species delivery system 130 may produce a desired concentration level of passivation species in the particle separation inlet 120. In one implementation, the concentration level may be the order of 0.005 to 400 parts per million (PPM), with the exact concentration level selected based upon the passivation species employed.

Selection of Passivation Species

The passivation species may be selected based on the sticky molecule being detected. In the case of $HNO_3$, it is desired that the passivation species be an acidic agent that has both an ability to eject $HNO_3$ from an interface, and an ability to inhibit further binding of the $HNO_3$ using a non-polar capping group. For example, PFHpA, PFOA, or PFBSA, or another species, may be selected as the passivation species for $HNO_3$ to provide these properties. For PFHpA and PFOA, the passivation species may be applied to achieve a concentration level on the order of 0.5-5 ppm in the particle separation inlet 120. For PFBSA, the passivation species may be applied to achieve a concentration level on the order of 0.05-0.5 ppm passivation in the particle separation inlet 120.

The ability to both eject $HNO_3$ and inhibit further binding of the $HNO_3$ may achieve a more desirable passivation agent than the mere presence of one or the other ability. $HNO_3$ ejection behavior may be nearly universal, for example, to carboxylic acids but only certain carboxylic acids may exhibit improved response time. If, for example, non-perfluorinated heptanoic acid is used as the passivation species, some ejection may be observed, but $HNO_3$ response time may not be improved. The perfluorination may be important for improving response time. Further, if perfluoroglutaric acid is used as the passivation species, some ejection may be observed, but $HNO_3$ response time may be slightly increased, leading to a worse result. A non-polar $CF_3$ capping group may therefore be important for improving response time.

A variety of other molecules with highly polar functional groups may not exhibit the same behavior as carboylic or sulfonic acids, and therefore may be unsuited for use as a passivation species for $HNO_3$. For example, hydroxyl and amide groups are also polar, with the latter being much more so than a carboxylic acid group (approximately 3.7 Debyes (D) vs. approximately 1.4-1.7 D, respectively). However, neither perfluorooctanol nor perfluorooctanamide may eject $HNO_3$ or reduce response times. One source of this difference may rest in the solubility of the —COOH and $-SO_3H$ groups vs. —OH and —$C(O)NH_2$ groups, where the former two can dissociate to ionic —$COO^-$ or —$SO_3^-$ states in the presence of surface water, while the latter two cannot. The $pK_a$ of long-chain perfluoroalkanoic acids in water is estimated to be approximately 0. While not strong acids, they are significantly more acidic than their non-perfluorinated counterparts, whose $pK_a$ values are approximately 4.75. Similarly, PFBSA has a $pK_a$ value of approximately −3. At the reasonably high concentrations that would be expected at an interface (approximately 1 M), these $pK_a$ values imply that a significant fraction of the carboxylic acid, and nearly all of the sulfonic acid, is dissociated. For comparison, $HNO_3$ dissociation at liquid water surfaces indicates that the $pK_a$ value of surface-bound $HNO_3$ is approximately −1 at bulk $HNO_3$ concentrations of 1 mol (M). The dissociation of the passivation species is therefore competitive with the surface-bound $HNO_3$ dissociation.

For $NH_3$ it is desired that the passivation species be a perfluorinated compound with a basic functional group. PFOAm or another species may be selected as the passivation species for $NH_3$ The basic amine group of PFOAm does not react with $NH_3$, yet can provide a surface passivation effect similar to the —COOH group of PFHpA. For PFOAm, the passivation species may be applied to achieve a concentration level on the order of 1-30 ppm in the particle separation inlet 120

It should be understood that for other sticky molecules being detected, a wide variety of other passivation species may be selected, and applied to achieve other concentration levels in the particle separation inlet 120.

Example Results

Application of a passivation species (either continuous or intermittent) may significantly improve response time of an output signal produced by a detector (e.g., MCT detector 118) to rapid changes in concentration. For example, in some cases, application of a passivation agent may decrease response time by more than a factor of 30 over operation without a passivation species.

FIG. 2A shows a graph 210 of typical $HNO_3$ response time using the example instrument 100 of FIG. 1, absent a passivation agent. The rise and fall times of $HNO_3$ may be best described by a double exponential in the form of $F(x)=y_0-A_1e^{-t/\tau 1}A_2e^{-t/\tau 2}$, with $\tau 1=1.38$ s and $\tau 2=39.9$ s, and $A_1/A_2=0.78$. The time required for the signal to achieve 75% and 90% of its final value after injection or removal of $HNO_3$ may be 32.3 second (s) and 68.9 s, respectively (such that $\tau_{75}=32.3$ s and $\tau_{90}=68.9$ s). Thus, the example instrument 100, absent application of a passivation species may be capable of seeing $HNO_3$ signals changing on the timescale of minutes. It may, however, be incapable of taking eddy covariance or taking plume transect-based measurements. Coating the particle separation inlet 120 with perfluorinated siloxanes in order to provide a non-stick interface may reduce the response time somewhat in the short term. However, as discussed above, the advantages of a coating are lost as dust, aerosols, or salts condense on the interfaces over time.

Figure 2B:
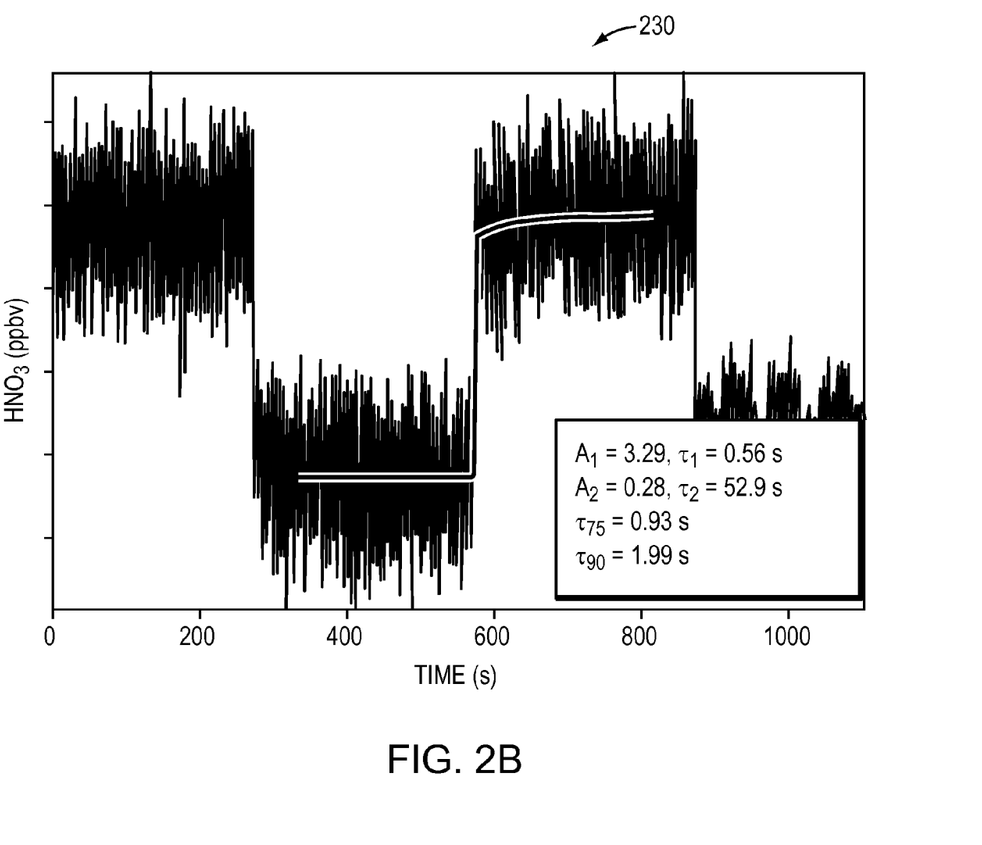
FIG. 2B shows a graph of example $HNO_3$ response time using the example instrument of FIG. 1, with continuous application of a passivation agent (in this example, PFHpA at concentrations of approximately 1.5 ppm)

FIG. 2B shows a graph 230 of example $HNO_3$ response time using the example instrument 100 of FIG. 1, with continuous application of a passivation agent (in this example, PFHpA at concentrations of approximately 1.5 ppm). The time required for the signal to achieve 75% and 90% of its final value after injection or removal of $HNO_3$ may be 0.93 s and 1.99 s (such that $\tau_{75}=0.93$ s and $\tau_{90}=1.99$ s), an improvement of more than a factor of 30. A similar improvement in response time may be observed when passivating with PFBSA. With PFBSA, it may be desirable to maintain concentrations below approximately 100 ppb, as above such level the reflectivity of the mirrors of the multi-pass absorption cell 116 may slowly decrease, indicating the formation of a non-reflective coating.

Figure 2C:
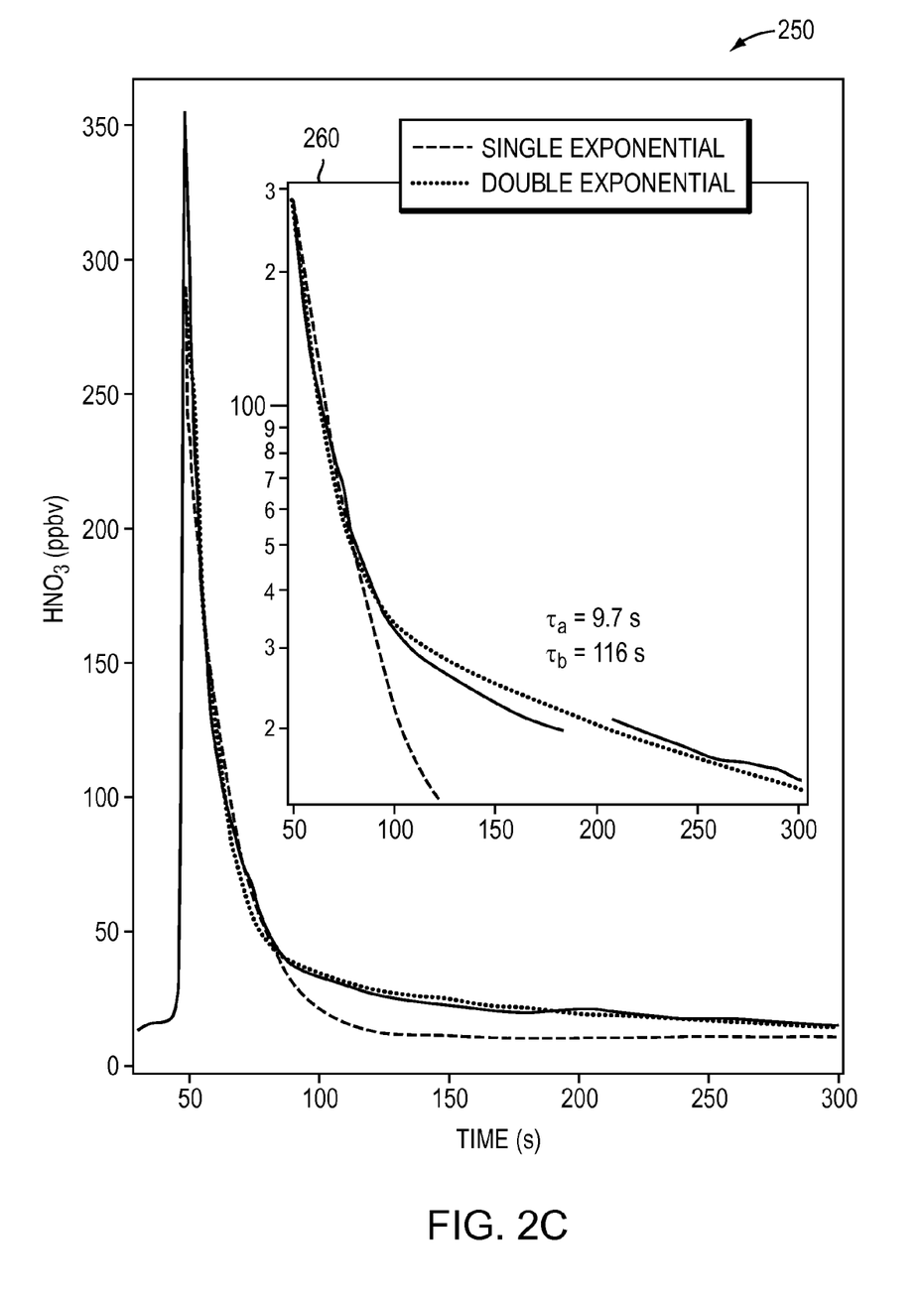
FIG. 2C shows a graph of example measured concentration of $HNO_3$ upon initial injection of a passivation agent (in this example, PFHpA)

FIG. 2C shows a graph 250 of example measured concentration of $HNO_3$ upon initial injection of a passivation agent (in this example, PFHpA). Approximately 1 ppm of PFOA is applied at 50 s. The $HNO_3$ signal rapidly increases to several hundred ppb before decaying down to its original level on a timescale of minutes. The insert 260 present a logarithmic scale emphasizing the double exponential nature of the decay. This same $HNO_3$ response may be observed when applying PFHpA or PFBSA. The passivation species is displacing a significant amount of adsorbed $HNO_3$. The qualitative character of the response is consistent with a two-step reaction sequence:

Where subscripts ad, g, and rem correspond to $HNO_3$ in the surface adsorbed state, the gas phase, and the removed (pumped out) state, respectively. In principle there is a reverse reaction, but given the fast pumping speed of the system and large passivation concentration (approximately1 ppm), the forward reaction dominates. The very rapid rise time in FIG. 2C indicates that the rate constant $k_2$ is large. Thus, the decay starting at approximately 50 s is dominated by the desorption rate constant $k_1$. This decay is best described by a double-exponential fit. This may be a reflection of two binding states of $HNO_3$ at the surface or two desorption mechanisms, and may be related to the double-exponential response in rise and fall times observed in FIGS. 2A and 2B.

Figure 3A:
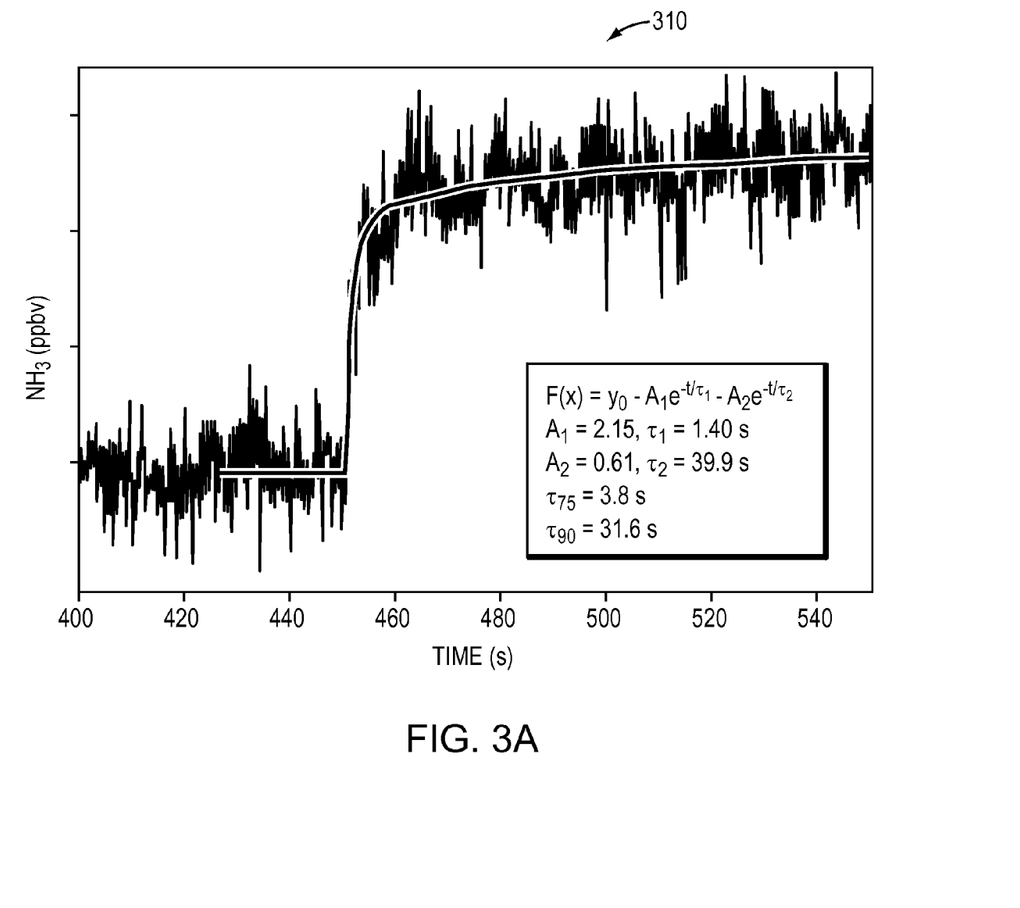
FIG. 3A shows a graph of typical $NH_3$ response time using the example instrument of FIG. 1, absent a passivation agent.

FIG. 3A shows a graph 310 of typical $NH_3$ response time using the example instrument 100 of FIG. 1, absent a passivation agent. The time required for the signal to reach achieve 75% and 90% of its final value after injection or removal of $HNO_3$ may be 3.8 s and 31.6 s (such that $\tau_{75}=3.8$ s and $\tau_{90}=31.6$ s) and $A_1/A_2=3.52$.

Figure 3B:
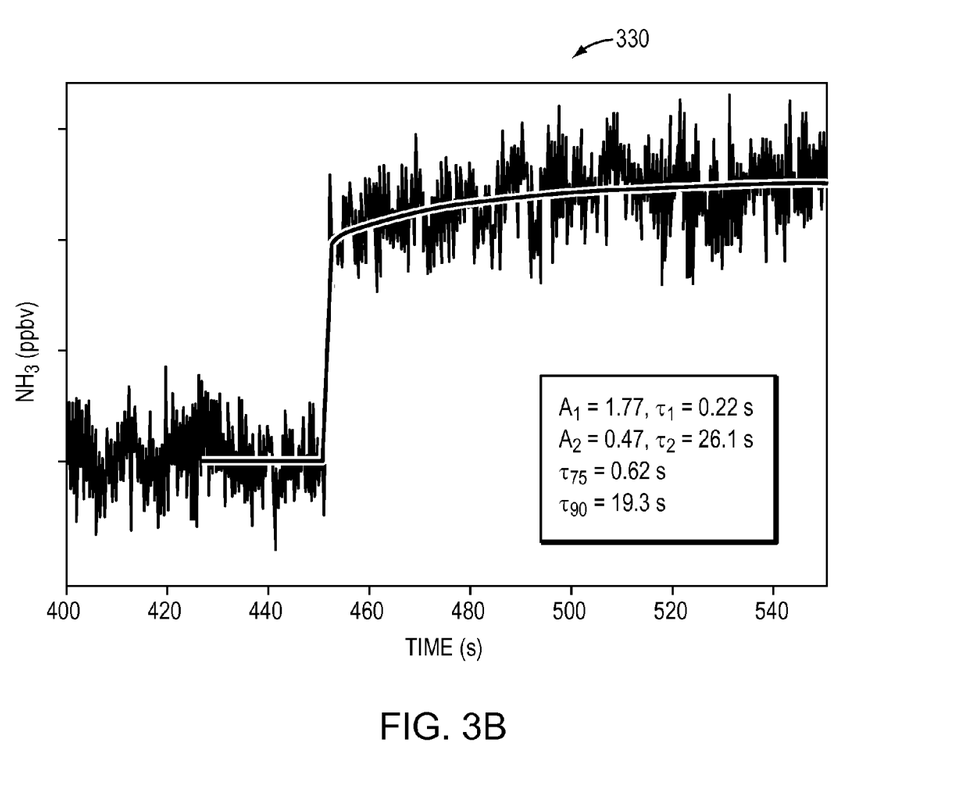
FIG. 3B shows a graph of example $NH_3$ response time using the example instrument of FIG. 1, with continuous application of a passivation agent (in this example, PFOAm at concentrations of approximately 1 ppm)

FIG. 3B shows a graph 330 of example $NH_3$ response time using the example instrument 100 of FIG. 1, with continuous application of a passivation agent (in this example, PFOAm at concentrations of approximately 1 ppm). Upon injection of PFOAm, the $NH_3$ mixing ratio exhibits a fast rise and double-exponential fall similar to that observed for $HNO_3$. The time required for the signal to reach achieve 75% and 90% of its final value after injection or removal of $NH_3$ may be 0.62 s and 19.3 s, respectively (such that $\tau_{75}=0.62$ s and $\tau_{90}=19.3$ s).

Figure 3C:
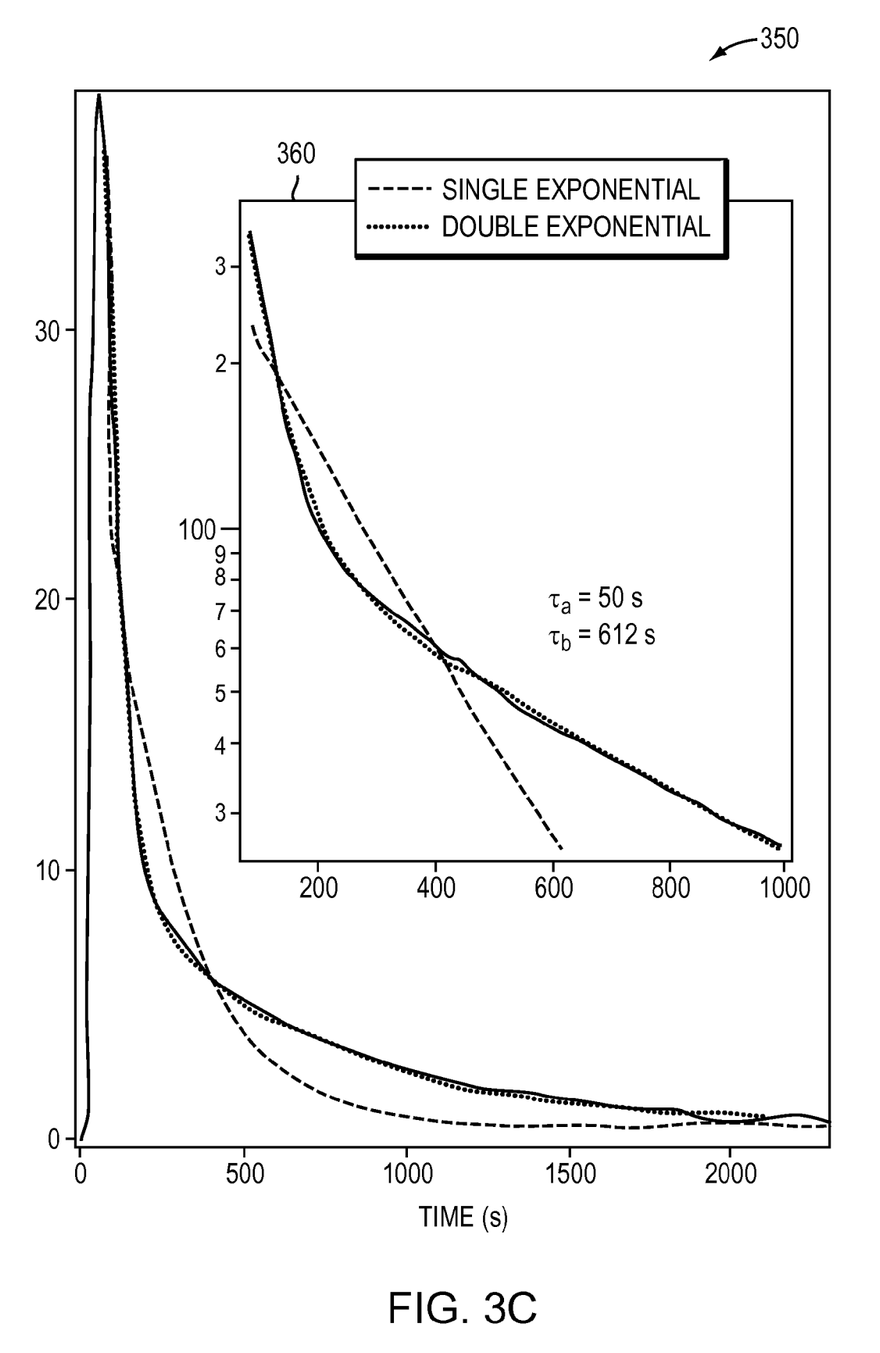
FIG. 3C shows a graph of example measured concentration of $NH_3$ upon initial injection of a passivation agent (in this example, PFOAm)

FIG. 3C shows a graph 350 of example measured concentration of $NH_3$ upon initial injection of a passivation agent (in this example, PFOAm). Approximately 15 ppm of PFOAm is applied at 10 s. The insert 360 present a logarithmic scale emphasizing the double exponential nature of the decay.

Production of a Long Lasting Coating

In some cases, where a passivation species is applied while large amounts of a sticky molecule are fed into the inlet, salt formation can occur, which may be observed as a film on the walls of the inlet. For example, if an acidic passivation species such as PFHpA or PFBSA is applied while large amounts (>5 ppbv) of $NH_3$ are continuously fed to the particle separation inlet 120, a low vapor pressure $NH_4^+/PFHpA^-$ or $NH_4^+/PFHSA^-$ salt can form on surfaces of the particle separation inlet 120 which may provide a long-lived protective coating. The protective coating may allow for continued fast response time for hours or days after passivation species application has been stopped.

Humidity Dependence

Active (continuous or intermittent) passivation may provide improved performance that is largely independent of humidity, in contrast to one-time PTFE or PFA surface coatings, where the response may be highly dependent upon relative humidity. The passivation species may not only eject sticky molecules at the interface, but may also eject water, or mitigate the effects of water, at the interface. The passivation species may mitigate the effect of water by binding to surface water molecules, for example, with a highly polar acid group, to prevent them from solvating the sticky molecule.

Figure 4:
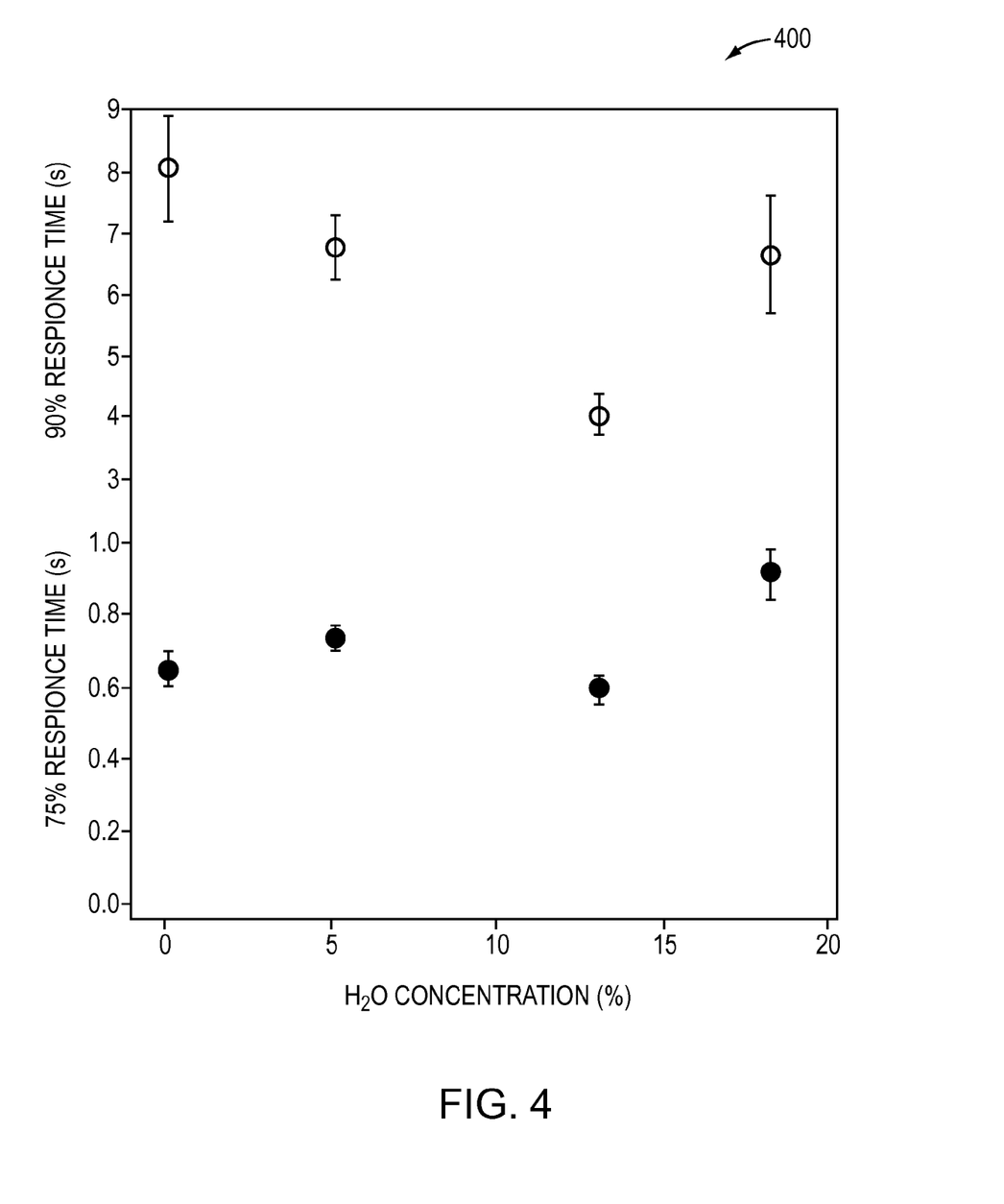
FIG. 4 is a graph that shows example time response based upon humidity for an example implementation where the passivation species is PFHpA and the sticky molecule is $HNO_3$.

FIG. 4 is a graph 400 that shows example time response based upon humidity for an example implementation where the passivation species is PFHpA and the sticky molecule is $HNO_3$. The error bars shown on each data point may correspond to a standard deviation of the mean over greater than 10 measurements of each data point. As can be seen 75% and 90% $HNO_3$ recovery times are largely independent of the humidity.

Summary of Process Steps

Figure 5:
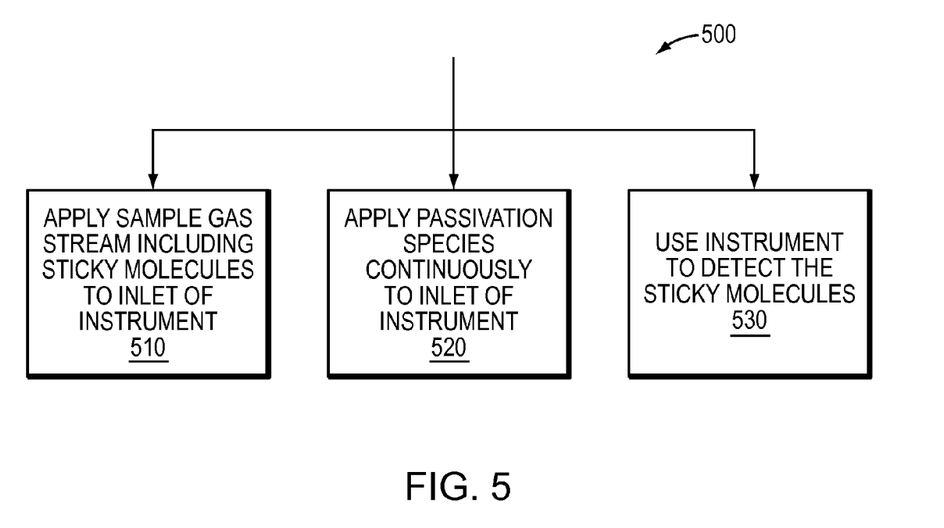
FIG. 5 is a flow diagram of an example sequence of steps for using continuous passivation to preventing interaction of sticky molecules with interfaces inside of an instrument.
Figure 6:
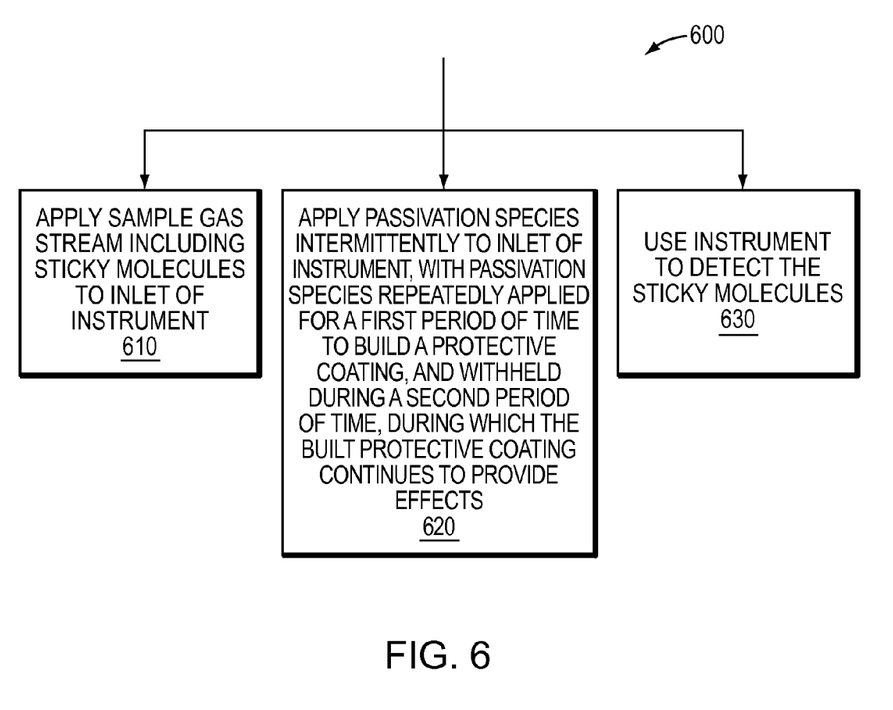
FIG. 6 is a flow diagram of an example sequence of steps for using intermittent passivation to preventing interaction of sticky molecules with interfaces inside of an instrument.

The above described techniques may be summarized as a sequence of process steps. FIG. 5 is a flow diagram of an example sequence of steps 500 for using continuous passivation to preventing interaction of sticky molecules with interfaces inside of an instrument (e.g., an infrared absorption spectrometer) 100. At step 510, a sample gas stream including the sticky molecules (e.g. $HNO_3$, $NH_3$, etc.) is applied to a particle separation inlet 120 of the instrument 100. At step 520, which may occur simultaneously to step 510, a passivation species (e.g., PFHpA, PFOA, PFBSA or another species in the case of $HNO_3$, PFOAm or another species in the case of $NH_3$, or yet another species in the case of other sticky molecules) is continuously applied to the particle separation inlet 120. The passivation species may have a polar functional group that binds to either water or polar groups of the interfaces, and once bound presents a non-polar group to prevent further binding of polar molecules. The passivation species may be applied in various ways. In one implementation, the passivation species may be introduced into a stream of air, for example by bubbling or passing the stream of air through a gas bubbler that contains the passivation species, and the stream of air may be entrained into the sample gas stream. In another implementation, the sample gas stream may be bubbled or passed through a gas bubbler that contains the passivation species. In still another implementation, the passivation species may be injected through a calibration port of the particle separation inlet 120. At step 530, which may occur simultaneously to steps 510 and 520, the instrument 100 is used to detect the sticky molecules.

FIG. 6 is a flow diagram of an example sequence of steps 600 for using intermittent passivation to preventing interaction of sticky molecules with interfaces inside of an instrument (e.g., an infrared absorption spectrometer). At step 610, a sample gas stream including the sticky molecules (e.g. $HNO_3$, $NH_3$, etc.) is applied to a particle separation inlet 120 of the instrument 100. At step 620, which may occur simultaneously to step 610, a passivation species (e.g., PFHpA, PFOA, PFBSA or another species in the case of $HNO_3$, PFOAm or another species in the case of $NH_3$, or yet another species in the case of other sticky molecules) is intermittently applied to the particle separation inlet 120, with the passivation species repeatedly applied for a first period of time (e.g., one or more hours or days) to build a protective coating on interfaces, and then withheld during a second period of time (e.g., one or more hours or days), during which the built protective coating continues to prevent interaction of sticky molecules with the interfaces. At step. 530, which may occur simultaneously to steps 510 and 520, the instrument is used to detect the sticky molecules.

In conclusion, the examples embodiments utilizing active (continuous or intermittent) passivation discussed above may be used to prevent interaction of sticky molecules with interfaces inside of an instrument. Where the instrument is used to detect the sticky molecules, improve response time when may be achieved. It should be understood that various aspects of the embodiments may be modified, added to, removed, or otherwise changed depending on the implementation. While the instrument 100 shown in FIG. 1, includes a detection system 130 including a multi-pass absorption cell 116 used to detect the sticky molecules, it should be understood that the techniques may be used with other types of instruments and equipment, that may be used for other purposes, and which may use another type of detection system 130, or may lack a detection system entirely. Further, while the instrument 100 shown in FIG. 1 includes a particle separation inlet 120, it should be understood that the techniques may be used with other types of inlets, which may not perform a particle separation function. In general, it should be understood that the above descriptions are meant to be taken only by way of example.

What is claimed is:

1. A method for preventing interaction of sticky molecules with interfaces inside of an instrument, comprising:

applying a sample gas stream including the sticky molecules to an inlet of the instrument;

while the sample gas stream is being applied, continuously applying a passivation species to the inlet, the passivation species being a species that includes a polar functional group that binds to either water or polar groups of the interfaces, and once bound presents a non-polar group to prevent further binding of polar molecules; and using the instrument to detect the sticky molecules while the passivation species is being applied to the inlet.

2. The method of claim 1, wherein the sticky molecules comprise nitric acid ($HNO_3$) and the passivation species comprises at least one of perfluoroheptanoic acid (PFHpA), perfluorooctanoic acid (PFOA) or perfluorobutane sulfonic acid (PFBSA).

3. The method of claim 1, wherein the sticky molecules comprise ammonia ($NH_3$) and the passivation species comprises 1H,1H-perfluorooctylamine (PFOAm).

4. The method of claim 1, wherein the inlet is a particle separation inlet that comprises a virtual impactor, a cyclone particle separator, or a PolyTetraFluoroEthylene (PTFE) membrane particle filter.

5. The method of claim 1, the method wherein the continuously applying comprises:

introducing the passivation species into a stream of air; and entraining the stream of air now including the passivation species into the sample gas stream.

6. The method of claim 5, wherein the introducing comprises:

bubbling or passing the stream of air through a bubbler that contains the passivation species.

7. The method of claim 1, the method wherein the continuously applying comprises:

injecting the passivation species through a calibration port of the inlet.

8. The method of claim 1, the method wherein the continuously applying comprises:

bubbling or passing the sample gas stream through a gas bubbler that contains the passivation species.

9. The method of claim 1, wherein the instrument is an infrared absorption spectrometer.

10. A method for preventing interaction of sticky molecules with interfaces inside of an instrument, comprising:

applying a sample gas stream including the sticky molecules to an inlet of the instrument;

while the sample gas stream is being applied, intermittently applying a passivation species to the inlet, the passivation species being a species that includes a polar functional group that binds to either water or polar groups of the interfaces, and once bound presents a non-polar group to prevent further binding of polar molecules, the passivation species applied for a first period of time to build a protective coating on the interfaces, and withheld during a second period of time during which the built protective coating continues to prevent interaction of sticky molecules with the interfaces; and using the instrument to detect the sticky molecules during the first period of time while the passivation species is being applied to the inlet and during the second period of time when the passivation species is withheld.

11. The method of claim 10, wherein the protective coating is a perfluoroheptanoic acid ammonium salt ($NH_4^+$/$PFHpA^-$) salt.

12. The method of claim 10, wherein the protective coating is a perfluorobutane sulfonic acid ammonium salt ($NH_4^+$/$PFBSA^-$).

13. The method of claim 10, wherein the instrument is an infrared absorption spectrometer and the inlet is a particle separation inlet.

14. The method of claim 10, the method wherein the intermittently applying comprises:

introducing the passivation species into a stream of air; and entraining the stream of air now including the passivation species into the sample gas stream.

15. An instrument configured to prevent interaction of sticky molecules with interfaces inside of the instrument, comprising: an inlet of the instrument configured to receive a sample gas stream including the sticky molecules; a passivation species delivery system coupled to the inlet and configured to apply a passivation species to the inlet while the inlet is receiving the sample gas stream, the passivation species being a species that includes a polar functional group configured to bind to either water or polar groups of the interfaces, and once bound presents a non-polar group to prevent further binding of polar molecules; and a detection system configured to receive a gas stream from the inlet and detect the sticky molecules while the passivation species is being applied to the inlet.

16. The instrument of claim 15, wherein the passivation delivery system is configured to apply the passivation species continuously to the inlet.

17. The instrument of claim 15, wherein the passivation delivery system is configured to apply the passivation species intermittently to the inlet such that the passivation species is applied for a first period of time to build a protective coating on the interfaces, and withheld during a second period of time during which the built protective coating continues to prevent interaction of sticky molecules with the interfaces.

18. The instrument of claim 15, wherein the sticky molecules comprise nitric acid ($HNO_3$) and the passivation species comprises at least one of perfluoroheptanoic acid (PFHpA), perfluorooctanoic acid (PFOA) or perfluorobutane sulfonic acid (PFBSA).

19. The instrument of claim 15, wherein the sticky molecules comprise ammonia ($NH_3$) and the passivation species comprises 1H,1H-perfluorooctylamine (PFOAm).

20. The instrument of claim 15, the wherein the passivation species delivery system comprises:
a gas bubbler that contains the passivation species through which a stream of air is bubbled or passed,
wherein the passivation species delivery system is configured to entrain the stream of air now including the passivation species into the sample gas stream.

21. The instrument of claim 15, wherein the instrument is an infrared absorption spectrometer and the inlet is a particle separation inlet.

22. The instrument of claim 15, the wherein the passivation species delivery system is configured to inject the passivation species through a calibration port of the inlet.

23. The instrument of claim 15, the wherein the passivation species delivery system includes a gas bubbler that contains the passivation species through which the sample gas is bubbled or passed.

* * * * *